(12) United States Patent
Chiao et al.

(10) Patent No.: US 6,375,618 B1
(45) Date of Patent: Apr. 23, 2002

(54) ENHANCED TISSUE-GENERATED HARMONIC IMAGING USING CODED EXCITATION

(75) Inventors: Richard Yung Chiao, Clifton Park, NY (US); Yasuhito Takeuchi, Tokyo (JP); Anne Lindsay Hall, New Berlin, WI (US); Kai Erik Thomenius, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/494,465

(22) Filed: Jan. 31, 2000

(51) Int. Cl.$^7$ .................................................. A61B 8/00
(52) U.S. Cl. ...................................................... 600/447
(58) Field of Search ................................ 600/443, 447; 73/625, 626; 128/916; 340/16 R; 367/7, 11, 103–105

(56) References Cited

U.S. PATENT DOCUMENTS 6,210,332 B1 * 4/2001 Chiao et al. ................. 600/447
6,213,947 B1 * 4/2001 Phillips ....................... 600/443
6,241,674 B1 * 6/2001 Phillips et al. .............. 600/443

OTHER PUBLICATIONS

Frank, "Polyphase Complementary Codes", IEEE Trans. Inform. Theory, vol. IT–26, No. 6, Nov. 1980, pp. 641–647.
Sivaswamy, "Multiphase Complementary Codes", IEEE Trans. Inform. Theory, vol. IT–24, No. 5, Sep. 1978, pp. 546–552.
Takeuchi, "An Investigation of a Spread Energy Method for Medical Ultrasound Systems. II. Proposed System and Possible Problems," Ultrasonic, vol. 17, Sep. 1979, pp. 219–224.
O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.
de Jong et al.., "Principles and Recent Developments in Ultrasound Contrast Agents," Ultrasonics, vol. 29, 1991, pp. 324–330.
Averkiou et al., "A New Imaging Technique Based on the Non–linear Properties of Tissue," Proc. 1997 IEEE Ultrason. Symp.
Uhlendorf, "Physics of Ultrasound Contrast Imaging: etc.," IEEE Trans. Ultrason. Ferroelec. & Freq. Control, vol. 41, No. 1, pp. 70–79, Jan. (1994).
Takeuchi, "Coded Excitation for Harmonic Imaging," Proc. 1997 IEEE Ultrasonics Symp., pp. 1433–1436.
Krishnan et al., "Transmit Aperture Processing for Non–Linear Contrast Agent Imaging," Ultrasonic Imaging, vol. 18, 1996, pp. 1–12 and 96–105.
"Barker Codes". U.S. Patent Application Serial No. 09/048, 760, Mar. 26, 1998.
"Golay Codes", U.S. Patent Application Ser. No. 09/063, 109, Apr. 20, 1998.
Welch et al., "Practical Spread Spectrum Pulse Compression for Ultrasonic Tissue Imaging," IEEE Trans. Ultrsonics, Ferroelect., and Freq. Control (accepted for publication, Aug. 1997).

* cited by examiner

*Primary Examiner*—Francis J. Jaworski
(74) *Attorney, Agent, or Firm*—Jill M. Breedlove; Christian G. Cabou (57) ABSTRACT

In performing tissue-generated harmonic imaging using coded excitation, the transmit waveform for acquiring the N-th harmonic signal is biphase (1,–1) encoded using two code symbols of a code sequence, the portions (i.e., chips) of the transmit waveform encoded with the second code symbol each being phase-shifted by 180°/N relative to the chips encoded with the first code symbol. This is implemented by time shifting the portions (i.e., chips) of the transmit sequence which are encoded with the second code symbol by ½N fractional cycle at center frequency relative to the chips of the transmit sequence encoded with the first code symbol. During reception, the desired harmonic signal is isolated by a bandpass filter centered at twice the fundamental frequency and enhanced with decoding.

26 Claims, 4 Drawing Sheets

ENHANCED TISSUE-GENERATED HARMONIC IMAGING USING CODED EXCITATION

FIELD OF THE INVENTION

This invention relates to ultrasound imaging systems and, more particularly, to increasing the harmonic-to-fundamental ratio and the harmonic-to-noise ratio of tissue-generated and contrast generated harmonic signals in medical ultrasound imaging.

BACKGROUND OF THE INVENTION

Conventional ultrasound imaging systems comprise an array of ultrasonic transducer elements for transmitting an ultrasound beam and receiving the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in focus or direction for each firing, e.g., by transmitting successive beams along the same scan line with the focal point of each beam being shifted relative to the focal point of the previous beam. For a steered array, by changing the time delays and amplitudes of the applied voltages, the beam with its focal point can be moved in a plane to scan the object. For a linear array, a focused beam directed normal to the array is scanned across the object by translating the aperture across the array from one firing to the next.

The same principles apply when the transducer probe is employed in a receive mode to receive the reflected sound. The voltages produced at the receiving transducer elements are summed so that the net signal is indicative of the ultrasound energy reflected from a single focal point in the object. As with the transmission mode, this focused reception of the ultrasonic energy is achieved by imparting separate time delays (and/or phase shifts) and gains to the signal from each receiving transducer element.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. After the transmission, one or more receive beamformers coherently sum the energy received by each channel, with dynamically changing phase rotation or time delays, to produce peak sensitivity along the desired scan lines at ranges proportional to the elapsed time. The resulting focused sensitivity pattern is referred to as a receive beam. A scan line resolution is a result of the directivity of the associated transmit and receive beam pair.

The output of the beamformer is detected to form a respective pixel intensity value for each sample volume in the object region or volume of interest. These pixel intensity values are log-compressed, scan-converted and then displayed as an image of the anatomy being scanned.

Conventional ultrasound transducers transmit a broadband signal centered at a fundamental frequency $f_0$, which is applied separately to each transducer element of the transmit aperture by a respective pulser. The pulsers are activated with time delays that produce the desired focusing of the transmit beam at a particular transmit focal position.

As the transmit beam propagates through tissue, echoes are created when the ultrasound wave is scattered or reflected from the boundaries between regions of different density. The transducer array transduces these ultrasound echoes into electrical signals, which are processed to produce an image of the tissue. These ultrasound images are formed from a combination of fundamental (linear) and harmonic (nonlinear) signal components, the latter of which are generated in nonlinear media such as tissue or a blood stream containing contrast agents. With scattering of linear signals, the received signal is a time-shifted, amplitude-scaled version of the transmitted signal. This is not true however for acoustic media which scatter nonlinear ultrasound waves.

The echoes from a high-amplitude signal transmission will contain both linear and nonlinear signal components. In some instances ultrasound images may be improved by suppressing the fundamental and emphasizing the harmonic (nonlinear) signal components. If the transmitted center frequency is $f_0$, then tissue/contrast nonlinearities will generate harmonics at $Nf_0$ and subharmonics at $f_0/N$, where N is an integer greater than or equal to 2. [The term "(sub) harmonic" refers to harmonic and/or subharmonic signal components.] Imaging of harmonic signals has been performed by transmitting a narrow-band signal at frequency $f_0$ and receiving at a band centered at frequency $2f_0$ (second harmonic) followed by receive signal processing.

Tissue-generated harmonic imaging is capable of greatly improving B-mode image quality in difficult-to-image patients. One problem faced by tissue-generated harmonic imaging is low harmonic-to-noise ratio (HNR) since the harmonic signals are at least an order of magnitude lower in amplitude than the fundamental signal. A secondary problem is insufficient isolation of the harmonic signal from the fundamental as measured by a low harmonic-to-fundamental ratio (HFR).

Coded excitation is a well-known technique in medical ultrasound imaging. For example, the use of Barker codes is disclosed in commonly assigned U.S. Pat. No. 5,938,611, issued Aug. 17, 1999 and the use of Golay codes is disclosed in commonly assigned U.S. Pat. No. 5,984,869, issued Nov. 16, 1999.

The techniques of tissue harmonic imaging and harmonic imaging using contrast agents are likewise known. The technique of tissue harmonic imaging is presented in Averkiou et al., "A New Imaging Technique Based on the Nonlinear Properties of Tissues," 1997 IEEE Ultrasonics Symp., pp. 1561–1566, while harmonic imaging using contrast agents is presented in de Jong et al., "Principles and Recent Developments in Ultrasound Contrast Agents," Ultrasonics, Vol. 29, 1991, pp. 324–330, and in Uhlendorf, "Physics of Ultrasound Contrast Imaging: Scattering in the Linear Range," IEEE Trans. Ultrason. Ferroelec. & Freq. Control, Vol. 41, No. 1, pp. 70–79, January (1994). Tissue harmonics can greatly improve B-mode image quality in difficult-to-image patients, while contrast harmonics can greatly improve vascular studies.

The technique of phase shifting the transmit signal across the transmit aperture to cancel out the transmitted signal at the second harmonic frequency is disclosed by Krishnan et al. in "Transmit Aperture Processing for Nonlinear Contrast Agent Imaging," Ultrasonic Imaging, Vol. 18, pp. 77–105, 1996.

Takeuchi has extended the phase shifting concept to coded excitation of contrast-generated second harmonic signals in "Coded Excitation for Harmonic Imaging," 1997 IEEE Ultrasonics Symp., pp. 1433–1436.

In medical ultrasound imaging systems of the type described hereinabove, it is desirable to optimize the HFR and HNR. In particular, there is a need for a system and a method for significantly increasing the HFR and HNR in harmonic imaging.

BRIEF SUMMARY OF THE INVENTION

In a preferred embodiment of the invention, performance of tissue-generated harmonic imaging using coded excitation improves the HFR and HNR of tissue-generated harmonic signals by transmitting a long encoded pulse sequence and decoding the received beamsummed data.

The transmitted pulse sequence amplitude is set sufficiently high to generate harmonic signals from the tissue nonlinearity. The harmonic signals are received (along with the fundamental signal), beamformed, isolated and decoded, and used to form an image.

In a preferred embodiment of the invention, the transmit waveform for acquiring the N-th harmonic signal is biphase (1,−1) encoded using two code symbols of a code sequence, each encoded portion (i.e., chip) of the transmit waveform encoded with the second code symbol being phase-shifted by 180°/N relative to the chips encoded with the first code symbol. This is implemented by time shifting the chips of the transmit sequence encoded with the second code symbol by ½N fractional cycle at center frequency relative to the chips encoded with the first code symbol. For the second harmonic signal (N=2), the phases of the two chips of the encoded transmit sequence are 90° apart, which is implemented by circularly shifting the second chip by a quarter cycle in the transmit sequence memory. [The term "circularly shifting" as used herein means that the time samples which are dropped at the front end of a shifted chip are added at the back end of the shifted chip.] During reception, the second harmonic signal is isolated by a bandpass filter centered at twice the fundamental frequency and enhanced with decoding. The bandpass filtering and decoding functions are preferably combined in one filter.

Increased HFR is realized since only the second harmonic signal is properly matched to the decoding filter while the fundamental (and other harmonics) are not properly encoded and do not achieve any decoding gain. Using this technique, both the HFR and HNR of the second harmonic signal increase by 10log(n) dB, where n is the number of chips in the single-transmit (e.g., Barker) code or by 10log(2n) for a two-transmit (e.g., Golay) code. The additional HFR gain allows broader-band signals to be used for improved resolution.

DETAILED DESCRIPTION OF THE PREFERRED EMBODIMENTS

Figure 1:
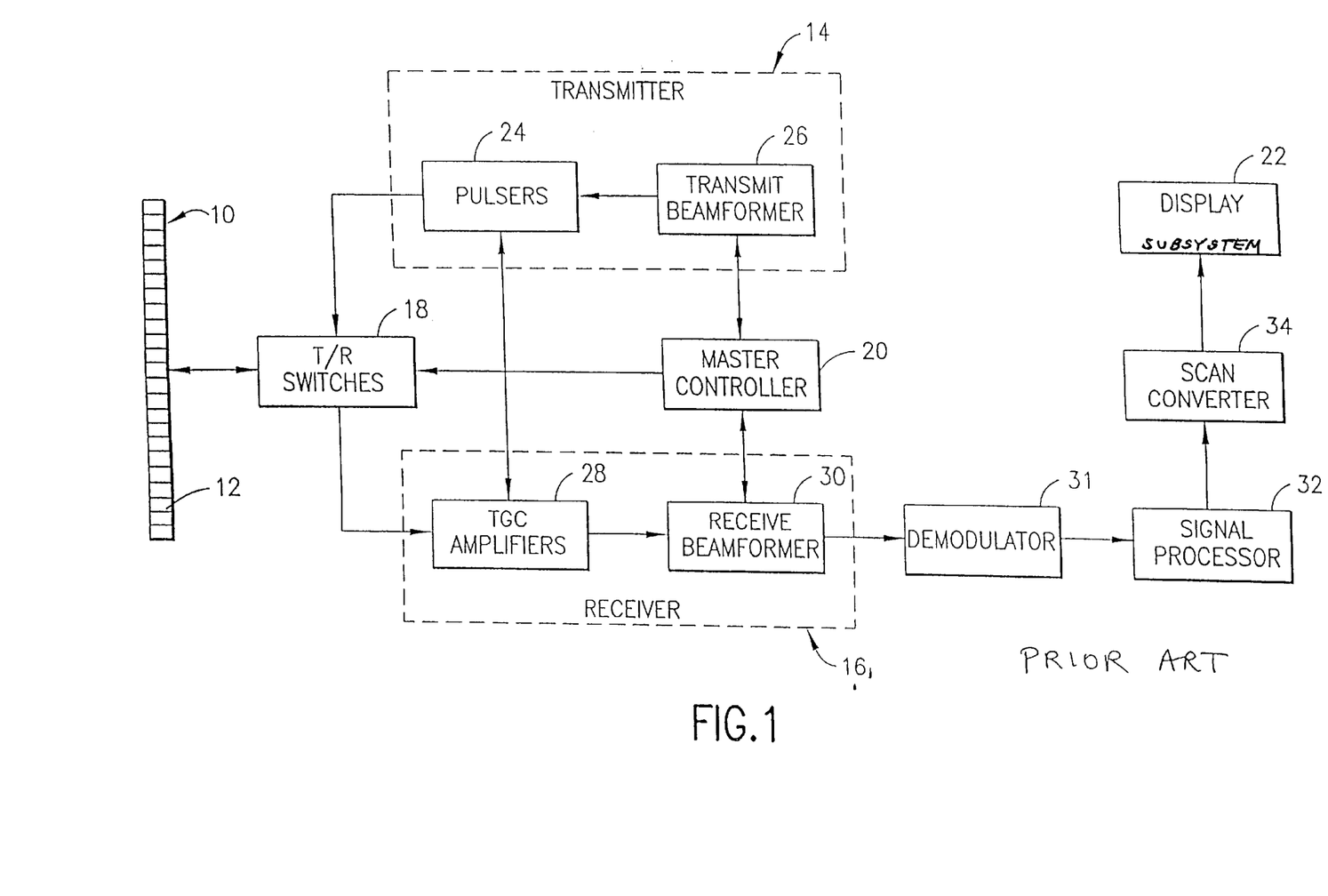
FIG. 1 is a block diagram of a conventional ultrasound imaging system.

One ultrasonic imaging system in which the present invention can be incorporated is depicted in FIG. 1. The system comprises a transducer array 10 having a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller (or host computer) 20 responsive to commands from a human operator via an operator interface (not shown). A complete scan is performed by acquiring a series of echoes after transmitter 14 has been gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal which is used to produce a line in an image on a video monitor of a display subsystem 22.

Under the direction of master controller 20, transmitter 14 drives transducer array 10 such that the ultrasonic energy is transmitted as a directed focused beam. To accomplish this, respective time delays are imparted to a multiplicity of pulsers 24 by a transmit beamformer 26. Master controller 20 determines the conditions under which the acoustic pulses will be transmitted. With this information, transmit beamformer 26 determines the timing and amplitude of each of the transmit pulses to be generated by pulsers 24. The amplitude of each transmit pulse is generated by an apodization generator (not shown). Pulsers 24 in turn send the transmit pulses to each of elements 12 of transducer array 10 via T/R switches 18, which protect time-gain control (TGC) amplifiers 28 from high voltages which may exist at the transducer array. By appropriately adjusting the transmit focus time delays and the apodization weightings in a conventional manner, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the echo signal magnitude at a particular point in time represents the amount of reflection occurring at a specific range. Due to differences in the propagation paths between a reflecting point and each transducer element 12, the echo signals are not detected simultaneously and their amplitudes are not equal. Receiver 16 amplifies the separate echo signals via a respective TGC amplifier 28 in each receive channel. Time-gain control is carried out by increasing or decreasing gain as a function of depth. The amount of amplification provided by the TGC amplifiers is controlled by a TGC driver circuit (not shown), that is set by the host computer and hand operation of potentiometers (not shown). The analog echo signals are then sent to receive beamformer 30.

Under the direction of master controller 20, receive beamformer 30 tracks the direction of the transmitted beam, sampling the echo signals at a succession of ranges along each beam. Receive beamformer 30 imparts the proper time delays and receive apodization weightings to each amplified echo signal and sums the signals to provide an echo signal which accurately indicates the total ultrasonic energy reflected from a point located at a particular range along one ultrasonic beam. The receive focus time delays are computed in real-time using specialized hardware or are read from a lookup table. The receive channels also have circuitry for filtering the received pulses. The filtered time-delayed receive signals are then summed.

In the system shown in FIG. 1, the frequency of the beamformer output signal is shifted to baseband by a demodulator 31. One way of achieving this is to multiply the input signal by a complex sinusoidal $e^{i2\pi f_d dt}$, where $f_d$ is the frequency shift required to bring the signal spectrum to baseband. The demodulated signals are provided to a signal processor 32 which converts the demodulated signals to display data. In the B-mode (gray-scale), the display data comprise the envelope of the signal with some additional processing, such as edge enhancement and logarithmic compression.

In general, the display data are converted by scan converter 34 into X-Y format for video display. The scan-converted frames are passed to a video processor (not shown) incorporated in display subsystem 22. The video processor maps the video data for display and sends the mapped image frames to the display subsystem.

The images displayed by the video monitor (not shown) of display subsystem 22 are produced from an image frame of data in which each datum represents intensity or brightness of a respective pixel in the display. An image frame may, e.g., comprise a 256×256 data array in which each intensity datum is an 8-bit binary number that represents pixel brightness. The brightness of each pixel on the video monitor is continuously refreshed by reading the value of its corresponding element in the data array in a well-known manner. Each pixel has an intensity value which is a function of the backscatter cross section of a respective sample volume in response to ultrasonic interrogating pulses.

Figure 2:
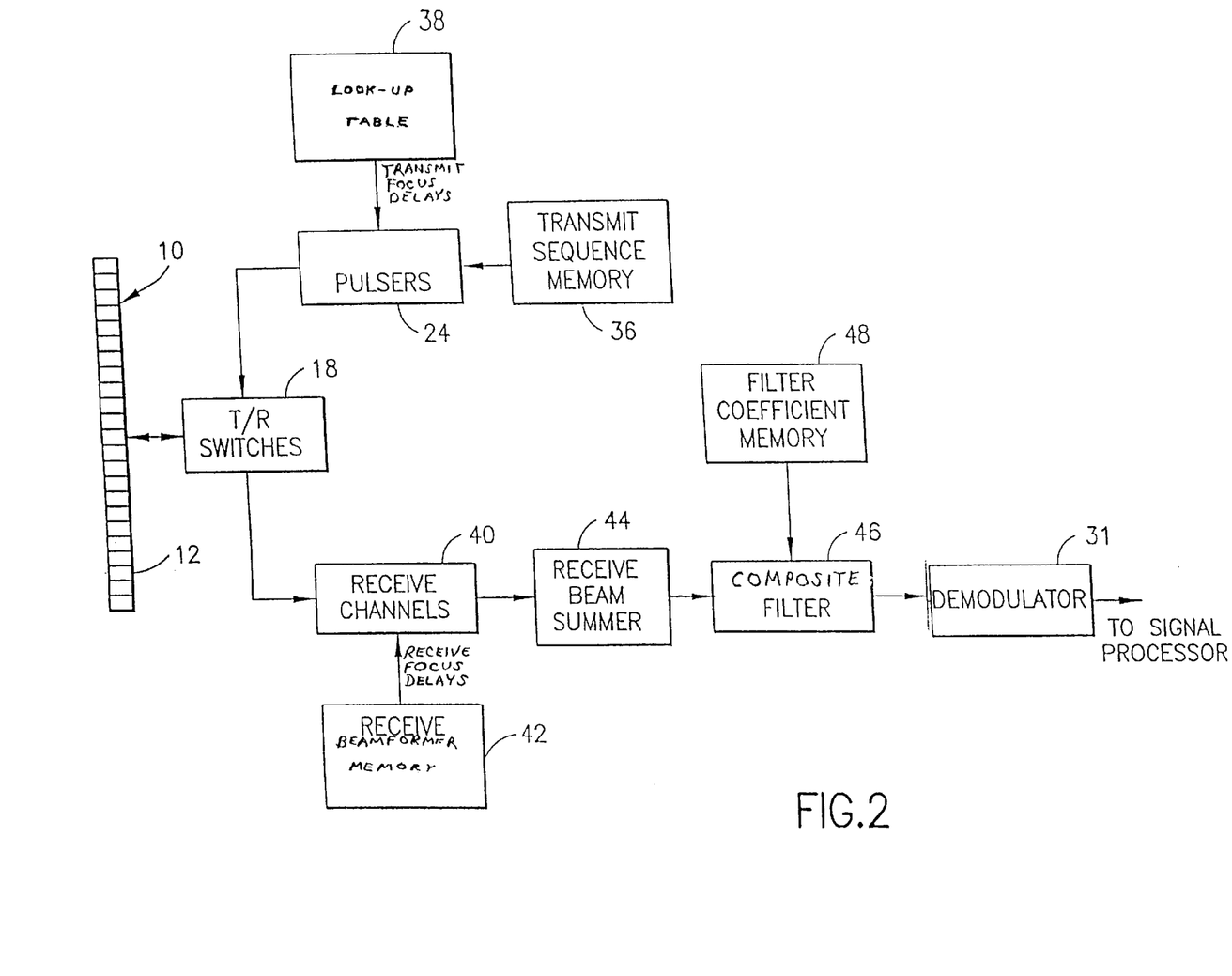
FIG. 2 is a block diagram of an ultrasound imaging system in accordance with a preferred embodiment of the invention.

FIG. 2 shows a preferred embodiment of the invention employing single-transmit coded excitation for the display of a harmonic image. In this system, each transducer element in the transmit aperture is pulsed using an encoded base sequence, each pulse in the sequence being commonly referred to as a chip. The encoded base sequence is formed by convolving a base sequence (comprising a sequence of +1 and −1 elements) with an oversampled code sequence (comprising an n-digit code, each digit being either of two code symbols, +1 and −1). In particular, the base sequence is phase encoded, using an n-digit code sequence, to create an n-chip encoded base sequence which is stored in a transmit sequence memory 36. When single-transmit codes (e.g., Barker codes) are employed, transmit sequence memory 36 stores one encoded base sequence for each transmit focal zone. When two-transmit codes (e.g., Golay codes) are employed, transmit sequence memory 36 stores two encoded base sequences for each transmit focal zone.

Figure 3:
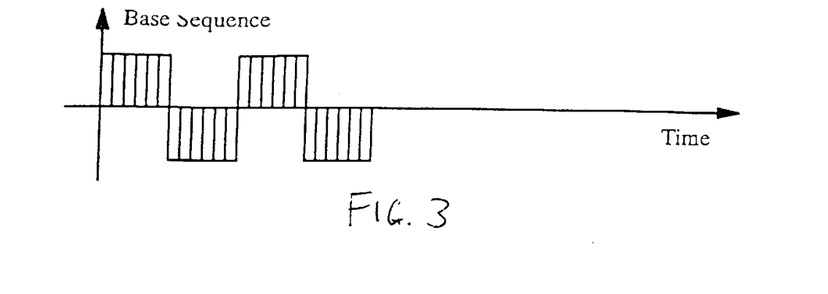
FIGS. 3–6 are pulse waveforms of one cycle of a base sequence (FIG. 3), an oversampled code sequence (FIG. 4), an encoded base sequence for fundamental imaging (FIG. 5), and an encoded base sequence for harmonic imaging in accordance with a preferred embodiment of the invention (FIG. 6).
Figure 4:
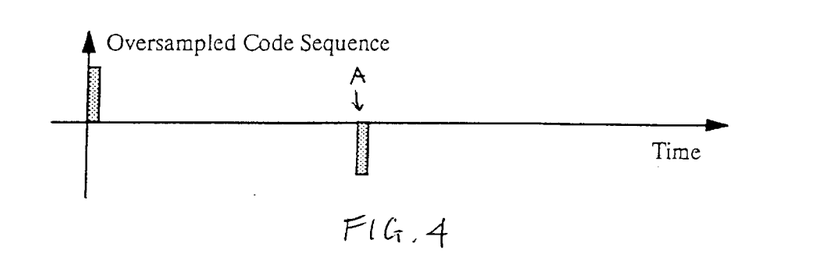
Figure 5:
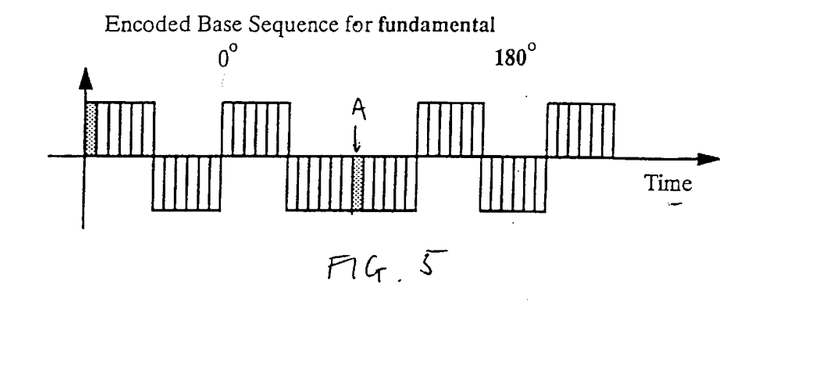
Figure 6:
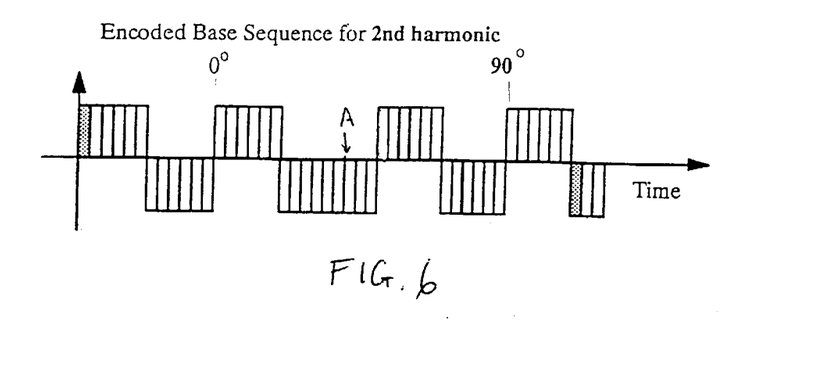

Generation of an exemplary encoded base sequence for use in harmonic imaging in accordance with a preferred embodiment of the invention is shown in FIGS. 3, 4 and 6. For comparison, FIG. 5 shows the corresponding encoded base sequence of the fundamental signal components for use in conventional imaging, wherein the code sequence is transmitted not directly but by oversampling (typically at 40 MHz or dt=0.025 μsec time samples) and then convolving the oversampled code sequence (shown in FIG. 4) with a base sequence (shown in FIG. 3) to form the encoded base sequence. The start of the base sequence encoded with the second code symbol of the code sequence is designated by the letter "A" in FIGS. 5 and 6. The encoded base sequence can be transmitted much more efficiently since its spectrum is better matched to the transducer passband with proper selection of the base sequence.

Conventional biphase codes, such as Barker and Golay codes, have two phase-inverted symbols such as +1 and −1. However, to encode the transmit waveform for acquiring the N-th harmonic signal using the code symbols of the code sequence shown in FIG. 4, the chips of the transmit waveform encoded with the second code symbol (i.e., −1) need to be phase-shifted by 180°/N relative to the chips encoded with the first code symbol (i.e., +1). This is because if the transmitted signal has a phase term exp[jθ], then the received N-th harmonic signal has a phase term exp[jNθ]. In particular, to encode the transmit waveform for acquiring the second (N=2) harmonic signal, the respective chips corresponding to the two code symbols +1 and −1 must be 90° apart in order for the respective second harmonic receive signals to be 180° apart. On receive, a bandpass filter at twice the fundamental center frequency isolates the second harmonic signal, which is subsequently decoded.

The phase shift in the encoded base sequence corresponding to the second code element is implemented by circularly shifting the corresponding chip in time by T=1/(2Nf$_0$) μsec, where N is the harmonic order and f$_0$ is the fundamental (i.e., transmit) center frequency in MHz. For example, for N=2 (second harmonic) and f$_0$=3.33 MHz, the time shift is T=0.075 μsec, which corresponds to T/dt=3 time samples. The chip in the encoded base sequence corresponding to a 90° phase shift is then circularly shifted in time by 3 time samples, the first of the 3 shifted time samples being shaded in FIG. 6. This is implemented by circularly shifting the second encoded base sequence (i.e., chip) by a quarter cycle in the transmit sequence memory.

In the system of FIG. 2, each encoded base sequence read out of transmit sequence memory 36 controls activation of a multiplicity of pulsers 24 during a respective transmit firing. The encoded base sequence for a given focal position is transmitted with sufficient amplitude such that harmonic signals are generated from nonlinear propagation in tissue. Pulsers 24 drive transducer elements 12 of transducer array 10 such that the ultrasonic energy produced is focused in a beam for each transmit firing. To accomplish this, transmit focus time delays from a look-up table 38 are imparted to the respective pulsed waveforms produced by the pulsers. By appropriately adjusting the transmit focus time delays in a conventional manner, the ultrasonic beams can be focused at a multiplicity of transmit focal positions to effect a scan in an image plane.

For each transmit, the echo signals from transducer elements 12 are fed to respective receive channels 40 of the receive beamformer. Each receive channel has a TGC amplifier and an analog-to-digital converter (not shown in FIG. 2). Under direction of master controller 20 (shown in FIG. 1), the receive beamformer tracks the direction of the transmitted beam. A receive beamformer memory 42 imparts the proper receive focus time delays to the received echo signals and thereafter sums the received echo signals to provide an echo signal that accurately represents the total ultrasonic energy reflected from a particular transmit focal position. The time-delayed receive signals are summed in a receive beamsummer 44 for each transmit firing.

For single-transmit coded excitation, the beamsummed receive signals acquired following the transmit firing are supplied to a composite filter 46, which correlates the beamsummed receive signal with a receive code. Composite filter 46 incorporates a bandpass filter centered at $Nf_0$ to isolate the N-th harmonic signal. Preferably, composite filter 46 comprises a finite impulse response (FIR) filter which performs both bandpass filtering and decode filtering. Suitable filter coefficients are stored in a filter coefficient memory 48 and are supplied to composite filter 46 at the appropriate times. It will be appreciated that separate filters, i.e., a bandpass FIR filter and a decoding FIR filter, can be substituted for a composite FIR filter. The bandpass FIR filter will have filter coefficients $b(m)$ designed to pass harmonic signal components, where $m=0,1,2,\ldots,(M-1)$, while the decoding FIR filter has filter coefficients $a(k)$ which are a function of the transmit code, where $k=0,1,2,\ldots,(K-1)$. The filter coefficients $c(i)$, where $i=0,1,2,\ldots,(MK-1)$, of a functionally equivalent composite FIR filter can be calculated by convolving the filter coefficients $a(k)$ with the filter coefficients $b(m)$ in accordance with the formula:

$$c(i) = \sum_{k=0}^{K-1} a(k)b(i-k) \qquad (1)$$

The bandpassed and decoded receive signal is demodulated by demodulator 31 and provided to signal processor 32 (see FIG. 1). In the B mode, signal processing includes envelope detection, edge enhancement and logarithmic compression. After signal processing and scan conversion, a scan line is displayed on the video monitor of the display subsystem. This procedure is repeated so that a respective scan line is displayed for each transmit focal position (in the instance of one transmit focal position for each beam angle) or for each vector (in the instance of multiple transmit focal positions for each beam angle), thereby forming a harmonic image of the desired order.

For biphase single-transmit codes (e.g., Barker codes), a specially designed code sequence modulates a transmit burst (base sequence) of length P. An encoded base sequence of n chips has a total length n×P. The beamformer output signal is compressed in time by passing through composite bandpass/decoding filter 46 (see FIG. 2). Some coded waveforms are best compressed by matched filtering, i.e., using a set of decode FIR filter coefficients $a(k)$ that is an identical copy of the n-chip transmit code. However, sometimes more desirable compression effects are achieved by mismatched filtering using FIR filters that have more than n filter coefficients or have coefficients which differ from the original n-chip transmit code. The output signal of composite filter 46 is a compressed-pulse harmonic signal of length equal to, or close to, the original transmit burst length P, but of amplitude n-times larger.

Figure 7:
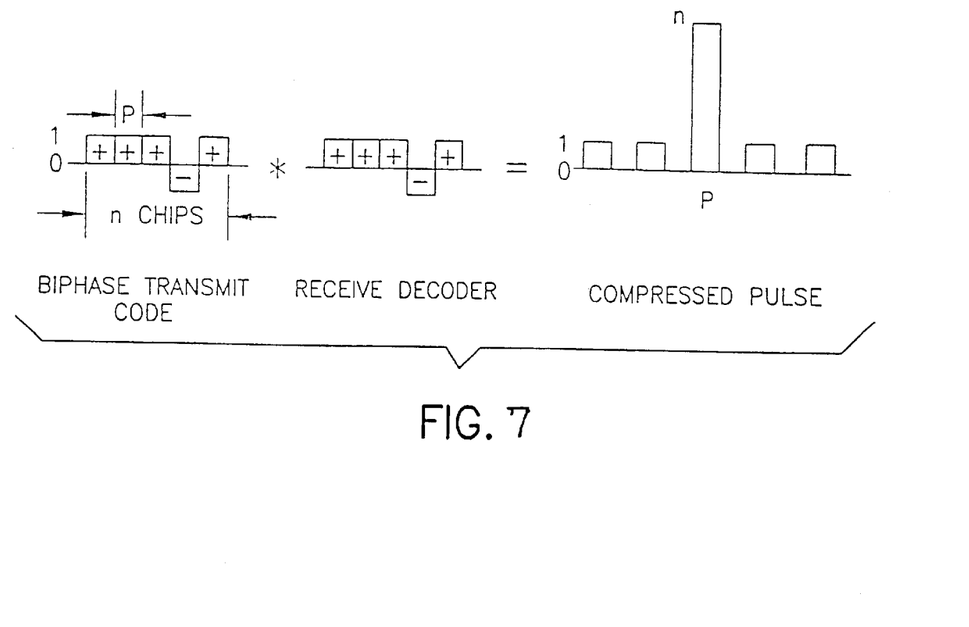
FIG. 7 is a schematic illustration of a compressed pulse resulting from convolution of a 5-bit biphase code sequence with matched filter coefficients of a decoding filter in accordance with an alternative preferred embodiment.

As an example, FIG. 7 shows a 5-chip code sequence from the Barker code family. Barker codes are biphase (or binary) code sequences of various lengths up to n=13. If the 5-bit Barker code [1,1,1,−1,1] is decoded by a matching FIR filter (i.e., a filter having filter coefficients identical to the digits of the transmit code) as shown in FIG. 7, the compression ratio achieved is n=5, which corresponds to a SNR gain of 7 dB. However, as seen in FIG. 7, the main pulse in the decoder filter output signal is surrounded by pulses of smaller amplitude. These smaller amplitude pulses correspond to axial or range sidelobes that are 1/n times lower in amplitude compared to the main lobe.

When separate bandpass and decoding filters are used, the decoding or autocorrelation is achieved on receive by the decoding filter. The appropriate decoding filter is designed based on the transmit code, the demodulation frequency (if decoding follows demodulation) and the amount of downsampling performed on receive.

Among all biphase codes, Barker codes are well known for their property of having the smallest sidelobes possible when decoded by a matched filter. However, for any single-transmit code, the sidelobes can often be suppressed via mismatched filtering at the expense of decreased signal gain and/or main lobe broadening (decreased range resolution). In general, greater sidelobe suppression can be achieved using longer mismatched FIR filters.

Figure 8:
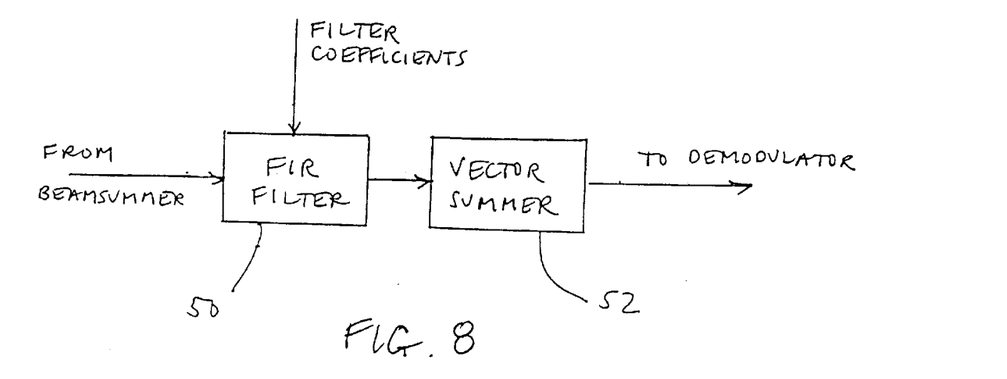
FIG. 8 is a block diagram of a filter in accordance with a preferred embodiment using a two-transmit (e.g., Golay) code.

For two-transmit codes (e.g., Golay), there are two encoded base sequences for each transmit focal zone. The encoded base sequences for a given focal position are transmitted with sufficient amplitude such that harmonic signals are generated from nonlinear propagation in tissue, and the received waveforms are beamformed, decoded, and used to form a harmonic image. For two-transmit codes, the decoding filter comprises an FIR filter and a vector summer. The output signal of the FIR filter is accumulated over the two transmits at a given focal position to complete the decoding step. FIG. 8 shows an FIR filter 50 which performs the function of bandpassing the desired harmonic signal component and then correlating each receive code with the respective transmit code. For the purpose of this application, the term "decoder" means hardware and/or software for performing the functions of filtering the receive vectors to pass a harmonic signal component, and decoding the receive vectors. In the embodiment depicted in part in FIG. 8, FIR filter 50 and vector summer 52 form a decoder. (In contrast, in the embodiment shown in FIG. 2, composite filter 46 forms the decoder.) During reception following the first coded transmit, composite FIR filter 50 filters a first beamsummed receive vector in accordance with a first set of filter coefficients determined by convolving filter coefficients for a harmonic bandpass filter with filter coefficients for a decoding filter which are matched to the first transmit code. The first filtered receive vector supplied by composite filter 50 is stored in a buffer memory in vector summer 52. During reception following the second coded transmit, composite FIR filter 50 filters a second beamsummed receive vector in accordance with a second set of filter coefficients determined by convolving the filter coefficients for the harmonic bandpass filter with filter coefficients for a decoding filter which are matched to the second transmit code. The second filtered receive vector is supplied to vector summer 52, where it is summed with the first filtered receive vector stored in buffer memory. The summed filtered (i.e., bandpassed and decoded) receive vector is then further processed for image display.

For two-transmit coded excitation, the transducer elements are pulsed in accordance with a first coded sequence during a first transmit firing focused at a desired transmit focal position and in accordance with a second coded sequence during a second transmit firing focused at the same transmit focal position. The first and second coded sequences are generated by respectively convolving first and second code sequences (e.g., Golay code pairs) with the base sequence, i.e., by phase encoding the base sequence using the code sequences. In accordance with a preferred embodiment, the first and second transmit codes are complementary Golay codes, e.g., the Golay code pair [1,1] and [1,-1], and pulsers 24 (see FIG. 2) are bipolar. In accordance with a preferred embodiment, each chip of the Golay-encoded base sequences which is encoded by the code symbol -1 is circularly time shifted by ½N fractional cycle relative to the chips encoded by the code symbol +1.

During each firing, pulsers 24 are excited by a Golay-encoded base sequence provided from transmit sequence memory 36 or from specialized hardware. In response to the Golay-encoded base sequence from transmit sequence memory 36 and the transmit focus delays provided from look-up table 38, the pulsers provide Golay-encoded pulse sequences to the respective transducer elements 12 making up the transmit aperture. The +1 and -1 symbols of each Golay-encoded base sequence are transformed into pulses of 0 and 90 degree phase by pulsers 24.

For each firing, bandpass filtering is performed at the second harmonic frequency and decode filtering is performed using the oversampled Golay sequences corresponding to the Golay-encoded base sequence employed during transmission. The time-reversed oversampled Golay sequences y(-k) are stored in filter coefficient memory 48 and are provided to FIR filter 50 (see FIG. 8) at the appropriate times. Filter 50 correlates the received signal x(k) with the oversampled Golay sequence y(k):

$$x(k) * \overline{y(-k)} = \sum_m x(m+k)\overline{y(m)} \quad (2)$$

where * denotes convolution and the overbar denotes conjugation (if x and y are complex). The results of the correlations are summed in vector summer 52 (see FIG. 8) to form the decoded signal, which is then provided to demodulator 31.

The imaging system incorporating the structure shown in FIG. 8 can also operate by demodulating the RF echo signals to baseband and downsampling before or after beamsummation. In this instance, the oversampled Golay sequences that are stored for correlation are also demodulated to baseband and downsampled.

The composite FIR filter can be implemented in software or hardware at the beamformer output, as shown in FIG. 2, or at the demodulator output. In the latter instance, the composite FIR filter coefficients must be matched or mismatched to the demodulated signals. For the situation when the demodulator shifts by discrete frequencies $f_d = k/2t_b$, where k is any positive integer and $t_b$ is the duration of the encoded base sequence, the sinusoidal becomes real and the same set of filter coefficients is applied to both composite filters for the I and Q components, which thus form a real filter. In the situation when $f_d \neq k/2t_b$, the I and Q composite filters receive different sets of filter coefficients and thus form a complex filter. In the latter situation, the filter coefficients are either matched or mismatched to the respective demodulated signal component.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for transmitting a beam of wave energy, comprising:
   a transducer array including a multiplicity of transducer elements;
   a multiplicity of pulsers coupled to respective transducer elements of said transducer array; and
   a transmit beamformer programmed to activate each of said pulsers with respective transmit focus delays and with an encoded base sequence during a transmit firing, said encoded base sequence comprising first and second chips formed by convolving a base sequence having a cycle with first and second code symbols respectively of a code sequence, said second chip being shifted relative to said first chip by ½N fractional cycle, where N is a positive integer greater than unity.

2. The system as recited in claim 1, wherein said first and second transducer elements comprise piezoelectric transducer elements.

3. The system as recited in claim 1, wherein said code sequence comprises a Barker code.

4. The system as recited in claim 1, wherein said transmit beamformer comprises a transmit sequence memory programmed with said encoded base sequence, said second chip comprising time samples which are circularly shifted by said ½N fractional cycle.

5. A method for operating a transducer array to transmit a beam of wave energy wherein transducer elements of said array form a transmit aperture, comprising the steps of driving each of said transducer elements with a coded excitation waveform during a transmit firing, said coded excitation waveform being encoded in accordance with an encoded base sequence comprising first and second chips formed by convolving a base sequence having a cycle with first and second code symbols respectively of a code sequence, said second chip being shifted relative to said first chip by ½N fractional cycle, where N is a positive integer greater than unity.

6. The method as recited in claim 5, wherein said code sequence comprises a Barker code.

7. An imaging system comprising:
   a transducer array including a multiplicity of transducer elements for transmitting wave energy in response to electrical activation and for transducing returned wave energy into electrical signals;
   a transmitter coupled to said transducer array and programmed to activate selected transducer elements to form a transmit aperture for transmitting focused wave energy having a fundamental frequency $f_0$ and encoded with an encoded base sequence during a transmit firing, said encoded base sequence comprising first and second chips formed by convolving a base sequence having a cycle with first and second code symbols respectively of a code sequence, said second chip being shifted relative to said first chip by ½N fractional cycle, where N is a positive integer greater than unity;
   a receiver programmed to form a receive vector from electrical signals provided from selected transducer elements forming a receive aperture subsequent to said transmit firing;
   a composite filter programmed to filter said receive vector as a function of said encoded base sequence and having a passband substantially centered at a harmonic frequency $Nf_0$; and a subsystem for displaying an image having an image portion which is a function of said filtered receive vector.

8. The system as recited in claim 7, wherein said code sequence comprises a Barker code.

9. The system as recited in claim 7, wherein said composite filter comprises an FIR filter.

10. The system as recited in claim 7, wherein said subsystem comprises:
a processing subsystem programmed to form an image signal from said filtered receive vector; and
a display subsystem programmed to display said image, having said image portion being a function of said image signal.

11. The system as recited in claim 7, wherein said transducer elements comprise piezoelectric elements for transmitting ultrasound waves in response to electrical activation and for transducing returned ultrasound waves into electrical signals.

12. An imaging system comprising:
a transducer array including a multiplicity of transducer elements for transmitting wave energy in response to electrical activation and for transducing returned wave energy into electrical signals;
a transmitter coupled to said transducer array and programmed to activate selected transducer elements to form a transmit aperture for transmitting focused wave energy having a fundamental frequency $f_0$ and encoded with an encoded base sequence during a transmit firing, said encoded base sequence comprising first and second chips formed by convolving a base sequence having a cycle with first and second code symbols respectively of a code sequence, said second chip being shifted relative to said first chip by ½N fractional cycle, where N is a positive integer greater than unity;
a receiver programmed to form a receive vector from electrical signals provided from selected transducer elements forming a receive aperture subsequent to said transmit firing;
means for decoding a harmonic signal component of said receive vector, said harmonic signal component having a center frequency substantially equal to $Nf_0$; and
a subsystem for displaying an image having a portion which is a function of said decoded harmonic signal component of said receive vector.

13. An imaging system comprising:
a transducer array including a multiplicity of transducer elements for transmitting wave energy in response to electrical activation and for transducing returned wave energy into electrical signals;
a display subsystem for displaying an image having an image portion which is a function of an image signal; and
a computer programmed to perform the steps of:
(a) activating a plurality of said transducer elements to transmit focused wave energy having a fundamental frequency $f_0$ and encoded with an encoded base sequence during a transmit firing, said encoded base sequence comprising first and second chips formed by convolving a base sequence having a cycle with first and second code symbols respectively of a code sequence, said second chip being shifted relative to said first chip by ½N fractional cycle, where N is a positive integer greater than unity;
(b) forming a receive vector from electrical signals provided from selected transducer elements forming a receive aperture subsequent to said transmit firing;
(c) decoding a harmonic signal component of said receive vector, said harmonic signal component having a center frequency substantially equal to $Nf_0$;
(d) forming an image signal from said harmonic signal component of said receive vector; and
(e) sending said image signal to said display subsystem.

14. The system as recited in claim 13, wherein said code sequence comprises a Barker code.

15. The system as recited in claim 13, wherein said computer comprises an FIR filter for performing the decoding step and a memory for storing a set of filter coefficients for programming said FIR filter, said set of filter coefficients being a function of said encoded base sequence and said center frequency of said harmonic signal component of said receive vector.

16. The system as recited in claim 13, wherein said transducer elements comprise piezoelectric elements for transmitting ultrasound waves in response to electrical activation and for transducing returned ultrasound waves into electrical signals.

17. A method of operating an imaging system comprising a multiplicity of transducer elements for transmitting wave energy in response to electrical activation and for transducing returned wave energy into electrical signals, and a display subsystem for displaying an image having a portion which is a function of an image signal, said method comprising the steps of:
(a) activating a plurality of said transducer elements to transmit focused wave energy having a fundamental frequency $f_0$ and encoded with an encoded base sequence during a transmit firing, said encoded base sequence comprising first and second chips formed by convolving a base sequence having a cycle with first and second code symbols respectively of a code sequence, said second chip being shifted relative to said first chip by ½N fractional cycle, where N is a positive integer greater than unity;
(b) forming a receive vector from electrical signals provided from selected transducer elements forming a receive aperture subsequent to said transmit firing;
(c) decoding a harmonic signal component of said receive vector, said harmonic signal component having a center frequency substantially equal to $Nf_0$;
(d) forming an image signal from said harmonic signal component of said receive vector; and
(e) sending said image signal to said display subsystem.

18. The method as recited in claim 17, wherein said code sequence comprises a Barker code.

19. An imaging system comprising:
a transducer array including a multiplicity of transducer elements for transmitting wave energy in response to electrical activation and for transducing returned wave energy into electrical signals;
a transmitter coupled to said transducer array and programmed to activate selected transducer elements to form a transmit aperture for transmitting focused wave energy having a fundamental frequency $f_0$ and encoded with first and second encoded base sequences during first and second transmit firings respectively, said first and second encoded base sequences each comprising first and second chips formed by convolving a base sequence having a cycle with respective code symbols of first and second code sequences respectively, said code symbols being acquired from a set comprising first and second code symbols, each of said chips encoded by said second code symbol being shifted relative to the chips encoded by said first code symbol by ½N fractional cycle, where N is a positive integer greater than unity;

a receiver programmed to form first and second receive vectors from electrical signals provided from selected transducer elements forming a receive aperture subsequent to said first and second transmit firings respectively;

a composite filter programmed to filter said first and second receive vectors as a function of said first and second encoded base sequences respectively, and having a passband substantially centered at a harmonic frequency $Nf_0$;

a summer for adding said first and second filtered receive vectors to form a decoded receive vector; and a subsystem for displaying an image having an image portion which is a function of said decoded receive vector.

20. The system as recited in claim 19, wherein said first and second code sequences form a Golay code pair.

21. An imaging system comprising:

a transducer array including a multiplicity of transducer elements for transmitting wave energy in response to electrical activation and for transducing returned wave energy into electrical signals;

a transmitter coupled to said transducer array and programmed to activate selected transducer elements to form a transmit aperture for transmitting focused wave energy having a fundamental frequency $f_0$ and encoded with first and second encoded base sequences during first and second transmit firings respectively, said first and second encoded base sequences each comprising first and second chips formed by convolving a base sequence having a cycle with respective code symbols of first and second code sequences respectively, said code symbols being acquired from a set comprising first and second code symbols, each of said chips encoded by said second code symbol being shifted relative to the chips encoded by said first code symbol by ½N fractional cycle, where N is a positive integer greater than unity;

a receiver programmed to form first and second receive vectors from electrical signals provided from selected transducer elements forming a receive aperture subsequent to said first and second transmit firings respectively;

means for decoding said first and second receive vectors to form a harmonic signal component having a center frequency substantially equal to $Nf_0$; and a subsystem for displaying an image having a portion which is a function of said harmonic signal component.

22. The system as recited in claim 21, wherein said first and second code sequences form a Golay code pair.

23. An imaging system comprising:

a transducer array including a multiplicity of transducer elements for transmitting wave energy in response to electrical activation and for transducing returned wave energy into electrical signals;

a display subsystem for displaying an image having an image portion which is a function of an image signal; and a computer programmed to perform the steps of:

(a) activating selected transducer elements forming a transmit aperture to transmit focused wave energy having a fundamental frequency $f_0$ and encoded with first and second encoded base sequences during first and second transmit firings respectively, said first and second encoded base sequences each comprising first and second chips formed by convolving a base sequence having a cycle with respective code symbols of first and second code sequences respectively, said code symbols being acquired from a set comprising first and second code symbols, each of said chips encoded by said second code symbol being shifted relative to the chips encoded by said first code symbol by ½N fractional cycle, where N is a positive integer greater than unity;

(b) forming first and second receive vectors from electrical signals provided from selected transducer elements forming a receive aperture subsequent to said first and second transmit firings respectively;

(c) decoding said first and second receive vectors to form a harmonic signal component having a center frequency substantially equal to $Nf_0$;

(d) forming an image signal from said harmonic signal component; and (e) sending said image signal to said display subsystem.

24. The system as recited in claim 23, wherein said first and second code sequences form a Golay code pair.

25. A method of operating an imaging system comprising a multiplicity of transducer elements for transmitting wave energy in response to electrical activation and for transducing returned wave energy into electrical signals, and a display subsystem for displaying an image having a portion which is a function of an image signal, said method comprising the steps of:

(a) activating selected transducer elements forming a transmit aperture to transmit focused wave energy having a fundamental frequency $f_0$ and encoded with first and second encoded base sequences during first and second transmit firings respectively, said first and second encoded base sequences each comprising first and second chips formed by convolving a base sequence having a cycle with respective code symbols of first and second code sequences respectively, said code symbols being acquired from a set comprising first and second code symbols, each of said chips encoded by said second code symbol being shifted relative to the chips encoded by said first code symbol by ½N fractional cycle, where N is a positive integer greater than unity;

(b) forming first and second receive vectors from electrical signals provided from selected transducer elements forming a receive aperture subsequent to said first and second transmit firings respectively;

(c) decoding said first and second receive vectors to form a harmonic signal component having a center frequency substantially equal to $Nf_0$;

(d) forming an image signal from said harmonic signal component; and (e) sending said image signal to said display subsystem.

26. The method as recited in claim 25, wherein said first and second code sequences form a Golay code pair.

* * * * *